United States Patent
Yin

(10) Patent No.: US 11,754,076 B2
(45) Date of Patent: Sep. 12, 2023

(54) MAGNETIC COUPLING SUSPENSION PUMP

(71) Applicant: SUZHOU SUPERMAG INTELLIGENT TECHNOLOGY CO., LTD, Jiangsu (CN)

(72) Inventor: Chengke Yin, Suzhou (CN)

(73) Assignee: SUZHOU SUPERMAG INTELLIGENT TECHNOLOGY CO., LTD, Jiangsu (CN)

( * ) Notice: Subject to any disclaimer, the term of this patent is extended or adjusted under 35 U.S.C. 154(b) by 194 days.

(21) Appl. No.: 17/288,193

(22) PCT Filed: Mar. 19, 2020

(86) PCT No.: PCT/CN2020/080097
§ 371 (c)(1),
(2) Date: Apr. 23, 2021

(87) PCT Pub. No.: WO2020/220857
PCT Pub. Date: Nov. 5, 2020

(65) Prior Publication Data
US 2021/0404473 A1 Dec. 30, 2021

(30) Foreign Application Priority Data
Apr. 29, 2019 (CN) .......................... 201910352084.8

(51) Int. Cl.
*F04D 13/02* (2006.01)
*F04D 13/06* (2006.01)
(Continued)

(52) U.S. Cl.
CPC ......... *F04D 13/027* (2013.01); *A61M 60/196* (2021.01); *A61M 60/216* (2021.01);
(Continued)

(58) Field of Classification Search
CPC ...... F04D 13/024; F04D 13/027; F04D 13/06; F04D 29/058; A61M 60/419
See application file for complete search history.

(56) References Cited

U.S. PATENT DOCUMENTS

2020/0018318 A1* 1/2020 Chen .................... A61M 60/10

FOREIGN PATENT DOCUMENTS

| CN | 207612184 U | 7/2018 |
|----|-------------|--------|
| CN | 208259961 U | 12/2018 |
| WO | 2019/044737 A1 | 3/2019 |

OTHER PUBLICATIONS

English Abstract for International Publication No. WO2019/044737A1 (shown in front page of International Publication).
(Continued)

*Primary Examiner* — Kenneth J Hansen
(74) *Attorney, Agent, or Firm* — Carter, DeLuca & Farrell LLP

(57) ABSTRACT

A magnetic coupling suspension pump includes a stator body and a rotor. The stator body includes a magnetic suspension stator assembly and a magnetic coupler stator assembly; the rotor includes a magnetic suspension rotor assembly and a magnetic coupler rotor assembly; the magnetic suspension stator assembly and the magnetic suspension rotor assembly constitute a magnetic suspension assembly, and the magnetic suspension assembly is configured to generate radial uni-polar magnetic poles and magnetic fields arranged along a circumferential direction, resulting in that the rotor suspends; and the magnetic coupler stator assembly and the magnetic coupler rotor assembly constitute a magnetic coupler assembly, and the magnetic coupler assembly is configured to generate radial non-zero even number of periodic magnetic poles and magnetic fields arranged along the circumferential direction, resulting in that the rotor rotates.

20 Claims, 5 Drawing Sheets

(51) Int. Cl.
    *F04D 15/00*     (2006.01)
    *F04D 29/42*     (2006.01)
    *A61M 60/814*     (2021.01)
    *A61M 60/419*     (2021.01)
    *A61M 60/422*     (2021.01)
    *A61M 60/216*     (2021.01)
    *A61M 60/196*     (2021.01)

(52) U.S. Cl.
    CPC ........ *A61M 60/419* (2021.01); *A61M 60/422* (2021.01); *A61M 60/814* (2021.01); *F04D 13/024* (2013.01); *F04D 13/06* (2013.01); *F04D 15/0094* (2013.01); *F04D 29/4293* (2013.01)

(56) References Cited

OTHER PUBLICATIONS

International Search Report issued in corresponding Appl. No PCT/CN2020/080097, dated May 29, 2020, including English language translation of International Search Report (6 pages).

\* cited by examiner

MAGNETIC COUPLING SUSPENSION PUMP

TECHNICAL FIELD

The present application relates to a field of magnetic suspension and pump, especially to a high efficiency magnetic coupling suspension pump for fluid transportation.

BACKGROUND

Pump is a basic device for fluid transportation. A traditional pump generally includes an electrical motor, a rotation shaft, a dynamic seal element for rotation shaft, an impeller fixed at an end of the rotation shaft and a volute. In an operation process of the pump, the dynamic seal element has some problems such as causing friction shear to the fluid, causing leakage, pollution or failure to the fluid, and so on. In the case of transporting sensitive fluid such as blood, protein macromolecular drug, ultra-clean raw material, fuel, etc., the friction shear caused by the dynamic seal element may damage effective components of the fluid. In the fields of artificial heart, nuclear energy, space and the like, leakage and pollution caused by seal failure are unacceptable.

In view of the shortcomings of the related art, the present disclosure discloses a magnetic coupling suspension pump which has a high drive efficiency, does not generate any mechanical contact between a rotor and a stator during operation, completely avoids the friction shear of the bearing, does not need any dynamic seal, effectively avoids leakage and pollution, and has a high reliability.

SUMMARY

A magnetic coupling suspension pump of the present disclosure includes a stator body and a volute comprising a rotor. The stator body comprises a magnetic suspension stator assembly and a magnetic coupler stator assembly, the rotor comprises a magnetic suspension rotor assembly and a magnetic coupler rotor assembly, the magnetic suspension stator assembly and the magnetic suspension rotor assembly constitute a magnetic suspension assembly, and the magnetic coupler stator assembly and the magnetic coupler rotor assembly constitute a magnetic coupler assembly. The magnetic suspension assembly generates radial uni-polar magnetic poles and magnetic fields arranged along a circumferential direction, and the magnetic coupler assembly generates radial periodic magnetic poles and magnetic fields arranged along the circumferential direction. The magnetic suspension assembly and magnetic coupler assembly enable the rotor to completely suspend and rotate in the volute of the stator body. The rotor is provided with an impeller configured to rotate with the rotor. The volute is provided with a fluid inlet and a fluid outlet. During a fluid flows in the volute, the fluid fills a space between the rotor and an inner wall of the volute and is pushed by the impeller fixed on the rotation rotor.

During the magnetic coupling suspension pump disclosed by the present disclosure works, the magnetic suspension assembly provides a stable control of five freedom degrees for the rotor through interaction forces of the magnetic fields. Among these five freedom degrees, two freedom degrees in inclination and one freedom degree in axial displacement of the rotor are passively stable, while two radial freedom degrees are actively controlled to be stable. In order to realize active control of the two radial freedom degrees of the rotor, the magnetic suspension stator assembly includes: a rotor position sensor to monitor the displacement of the rotor in real time; a control circuit to generate a current in a coil of the magnetic suspension stator assembly according to the displacement of the rotor, thus realizing stable and controllable rotor magnetic suspension. The control circuit implements a zero power consumption control manner and a periodic zero power consumption control manner, which reduces power consumption of the magnetic suspension. The magnetic coupler assembly provides the rotor with torque required for rotation through interaction torque of the magnetic fields.

During the rotor rotates, all six freedom degrees of the rotor is under control of magnetic suspension and the electrical motor, the rotor rotates within a set position range of the stator body and the volute, to drive the impeller to rotate together and push the fluid in the volute to move. The rotor and impeller are completely and only immersed in the fluid in the volute, and there is no friction between the rotor, the impeller and other components and the components of the stator body during the rotation of the rotor and the impeller, thus completely avoiding any dynamic seal structure.

The volute and the stator body are configured to be separable from each other, and the volute can be conveniently replaced if needed, which is convenient for use and saves cost.

During the rotor rotates stably, the power consumption of magnetic suspension is very low. The magnetic coupler has no energy loss in a process of torque transmission. Therefore, almost all output power of the electrical motor is used to drive the fluid, and the efficiency of the whole machine is very high.

Optionally, the magnetic coupler the stator assembly is replaced by an electrical motor stator winding wound with multiphase coils to meet the requirement of special circumstances.

DETAILED DESCRIPTION

The specific embodiments of the present disclosure are further described in detail with reference to the drawings and examples. The following embodiments serve to illustrate the present disclosure, but are not intended to limit the scope of the present disclosure.

Figure 1:
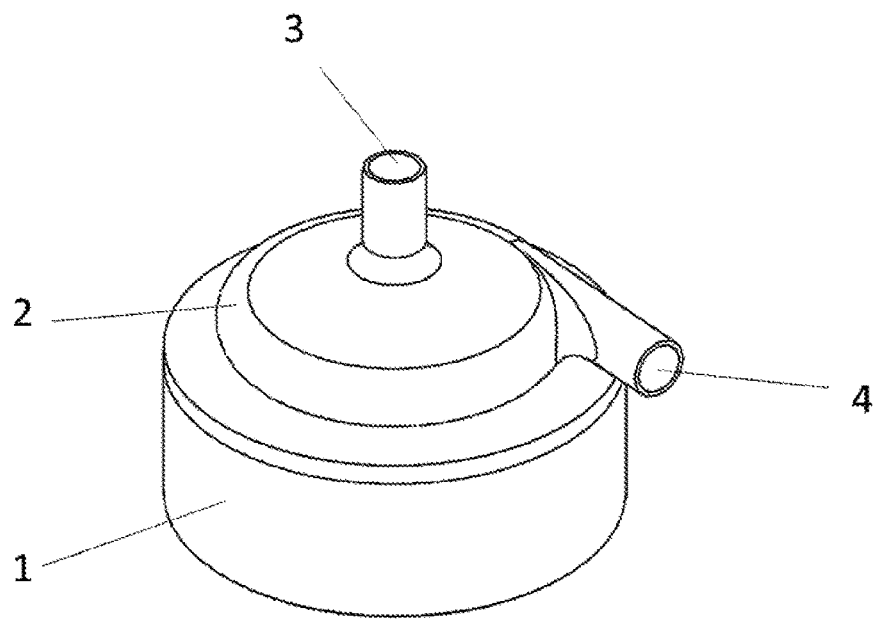
FIG. 1: an overall structure
Figure 2:
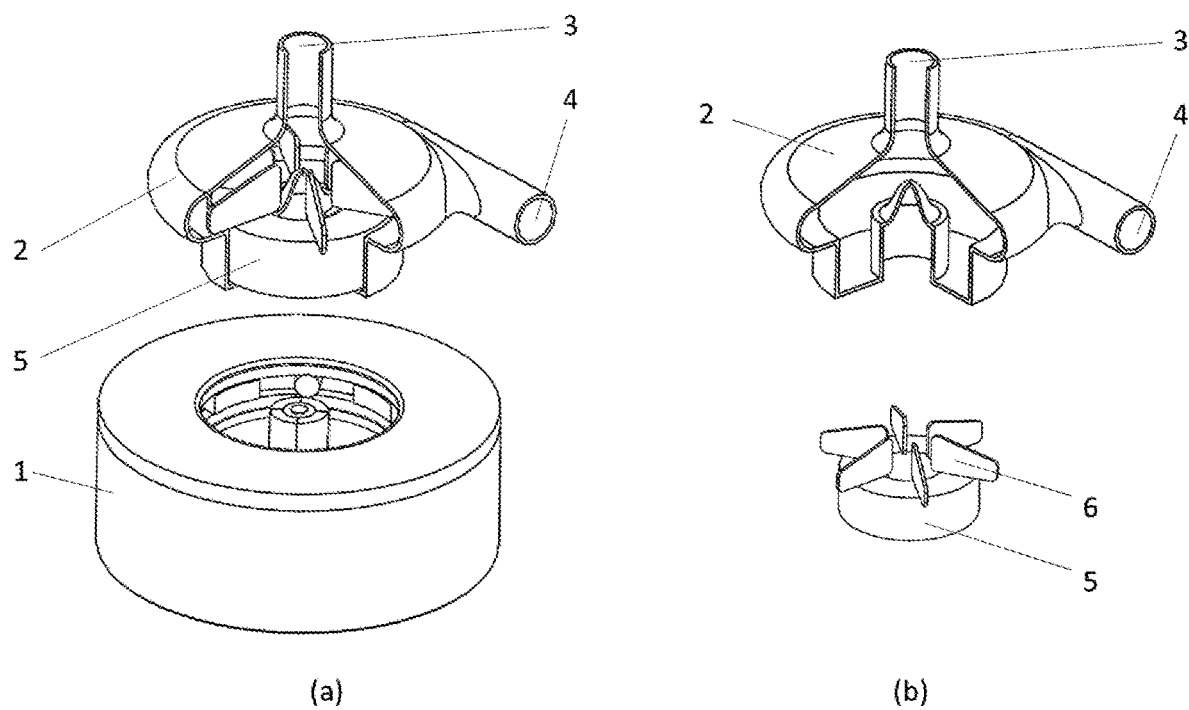
FIG. 2: respective components

As illustrated in FIG. 1, the magnetic coupling suspension pump disclosed by the present disclosure comprises a stator body 1 and a volute 2. The volute 2 is provided with a fluid inlet 3 and a fluid outlet 4. For example, the volute 2 and the stator body 1 are configured as an integral structure, or the volute 2 and the stator body 1 are configured to be separable from each other. FIG. 2(*a*) shows a rotor 5 in the volute 2, and FIG. 2(*b*) further respectively shows the rotor 5 in the volute 2 and an impeller 6 fixed on the rotor 5. The volute 2 is provided with the fluid inlet 3 and the fluid outlet 4. In the case that a fluid flows inside the volute 2, the fluid fills a space between the rotor 5 and an inner wall of the volute 2, and is pushed by the impeller 6 fixed on the rotating rotor 5.

During the magnetic coupling suspension pump works, the volute 2 is connected to the stator body 1, and the rotor 5 and the impeller 6 in the volute 2 stably suspend and rotate under an action of a magnetic field generated in combination with the stator body 1, and push the fluid in the volute 2 to move. During the rotor 5 and the impeller 6 rotate, the rotor 5 and the impeller 6 are completely suspended and immersed in the fluid inside the volute 2, and do not have any mechanical contact and friction with the volute 2, thus completely avoiding any mechanical bearing and any dynamic seal.

Figure 3:
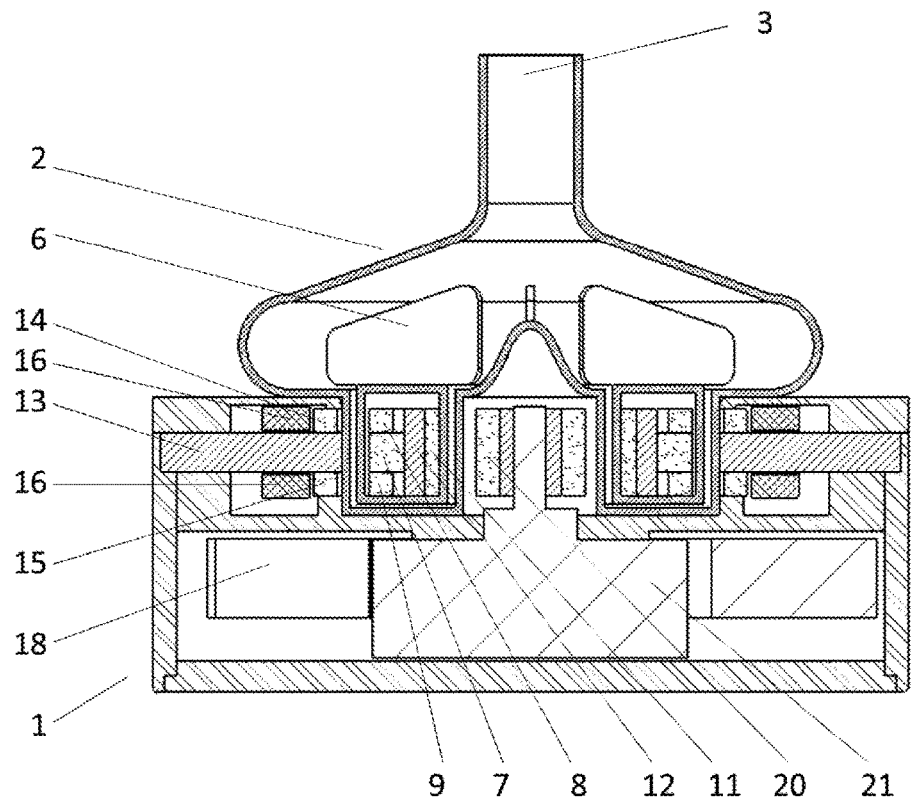
FIG. 3: an overall sectional view

The key of the present disclosure lies in how to enable the rotor 5 to stably suspend and rotate in the volute 2 and the stator body 1. FIG. 3 is a sectional view of the overall structure of the magnetic coupling suspension pump. The working principle of the magnetic coupling suspension pump is explained in detail below.

Figure 4:
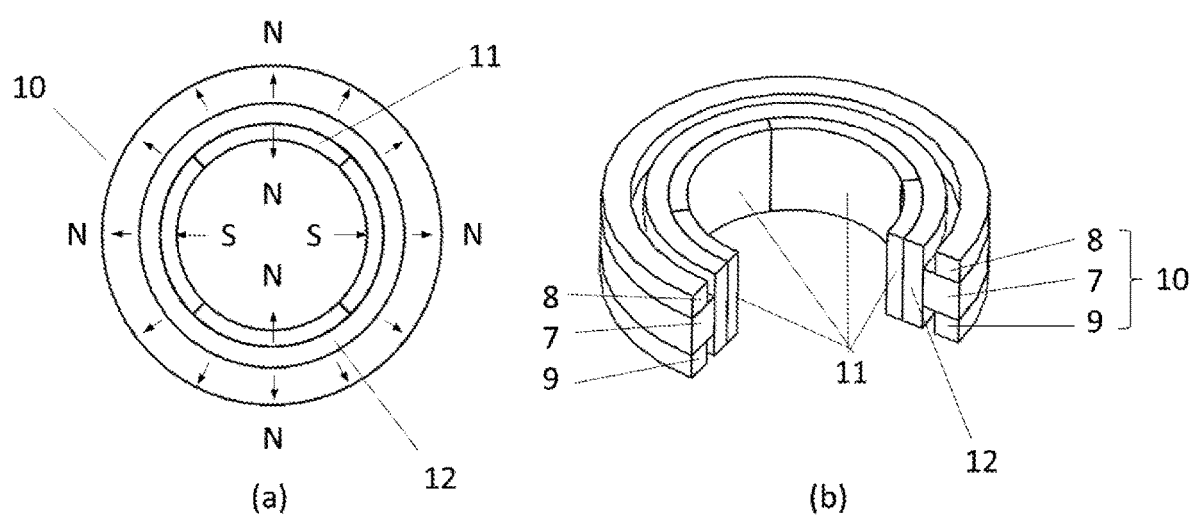
FIG. 4: a rotor

FIG. 4 (*a*) and FIG. 4 (*b*) show core components related to magnetic suspension and rotation, omitting unimportant parts such as impeller 6, of the rotor 5. The core components include: a magnetic suspension rotor assembly 10 including a magnetic ring 7, an auxiliary magnetic ring 8 and an auxiliary magnetic ring 9; a magnetic coupler rotor assembly 11 including a plurality of circumferentially-arranged fan-shaped magnets; and a magnetic conduction ring 12. Each magnetic ring of the magnetic suspension rotor assembly 10 is made of a permanent magnet material. A magnetization direction of the magnetic ring 7 is along a radial direction outwardly, a magnetization direction of the auxiliary magnetic ring 8 is along an axial direction upwardly, and a magnetization direction of the auxiliary magnetic ring 9 is along the axial direction downwardly. The axial direction herein refers to a direction of the only symmetry axis of the rotor 5 (the symmetry axis of the rotor 5 is the rotation axis of the rotor 5), and the radial direction herein refers to a direction of the radius of the rotor 5 in a plane perpendicular to the rotation axis of the rotor 5. The magnetic suspension rotor assembly 10 has the characteristics that magnetic poles of the magnetic suspension rotor assembly 10 are arranged as radial uni-polar magnetic poles, and magnetic fields generated by the magnetic poles of the magnetic suspension rotor assembly 10 are radial uni-polar magnetic fields, that is, an N-pole is on an outer side in the radial direction and an S-pole is on an inner side in the radial direction, or conversely, the S-pole is on the outer side in the radial direction and the N-pole is on the inner side in the radial direction. Based on this design of radial uni-polar magnetic field, there are many examples of the magnetic suspension rotor assembly 10, and several typical examples will be explained later in this disclosure.

The magnetic coupler rotor assembly 11 comprises the plurality of fan-shaped permanent magnets arranged in an array along a circumferential direction; the magnetization and arrangement mode of the magnetic coupler rotor assembly 11 have characteristics that magnetic poles of the magnetic coupler rotor assembly 11 are arranged as radial multi-polar magnetic poles, to form circumferentially-arranged multi-polar periodic magnetic fields. In order to generate the circumferentially-arranged multi-polar periodic magnetic fields, the magnetization direction of each fan-shaped permanent magnet is along the radial direction, and the magnetization directions of the plurality of fan-shaped permanent magnets are arranged periodically in a form of NSNS for example as viewed along the radial direction outwardly, and the magnetization directions of two adjacent magnets rotate 180 degrees with respect to each other. FIG. 4 shows an example of using four fan-shaped magnets to generate two pairs of radial magnetic poles and generate the periodic magnetic fields arranged along the circumferential direction. Obviously, it is possible to set any other non-zero even number of magnetic poles to generate the periodic magnetic fields.

Optionally, the plurality of fan-shaped magnets of the magnetic coupler rotor assembly 11 for example adopt an arrangement mode called Halbach array, in which the magnetization directions of two adjacent magnets rotate 90 degrees with respect to each other, that is, the magnets are arranged periodically in a magnetization mode of ↑ → ↓ ← ↑ → ↓ ← . . . , which generates periodic multi-polar magnetic fields that are superimposed to be enhanced on one side of the magnetic coupler rotor assembly while are superimposed to be weakened on the other side of the magnetic coupler rotor assembly, thus improving the utilization ratio of the magnets.

The magnetic conduction ring 12 is a back iron of the magnetic suspension rotor assembly 10 and the magnetic coupler rotor assembly 11, provides a closed loop respectively for the magnetic flux of the magnetic suspension rotor assembly 10 and the magnetic flux of the magnetic coupler rotor assembly 11, and isolates the magnetic field of the magnetic suspension rotor assembly 10 from the magnetic field of the magnetic coupler rotor assembly 11 so that they do not interfere with each other.

Figure 5:
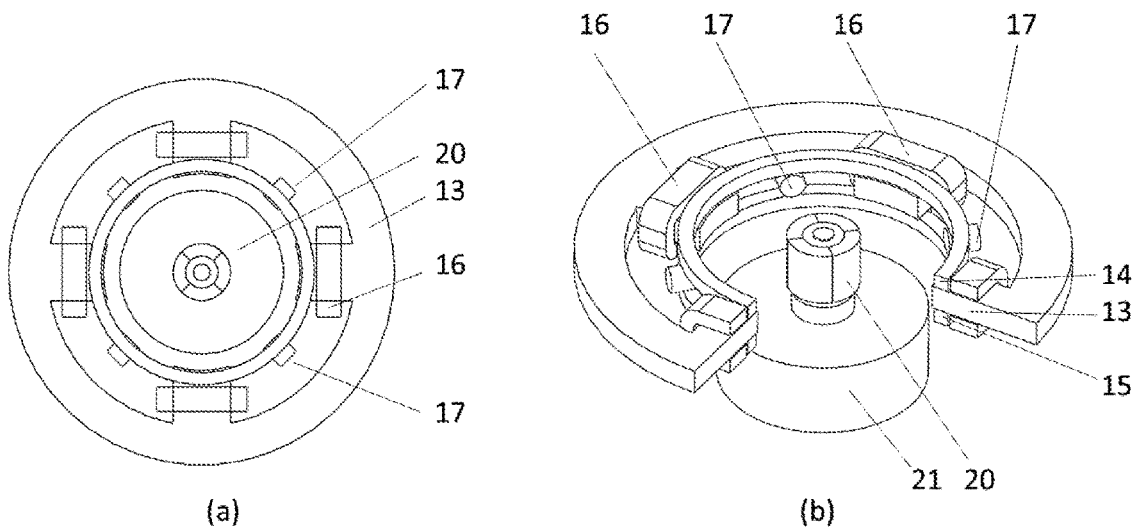
FIG. 5: a stator

FIG. 5 (*a*) and FIG. 5 (*b*) show core components related to magnetic suspension function and rotation function, omitting unimportant parts, of the stator body 1. The core components include: a magnetic suspension stator assembly 19 including a stator core 13, an auxiliary magnetic ring 14, an auxiliary magnetic ring 15, a coil 16, a rotor position sensor 17 and a control circuit 18; a magnetic coupler stator assembly 20 including fan-shaped magnets arranged in an array; and an electrical motor 21. The control circuit 18 is illustrated in FIG. 3.

The function of the magnetic suspension stator assembly 19 is to enable the rotor 5 to suspend stably. The rotor position sensor 17 detects a relative displacement between the rotor 5 and the stator body 1, and the control circuit 18 calculates and controls the magnitude and direction of the current in the coil 16 according to the displacement, so that a magnetic field is generated in the stator core 13 and the magnetic field generates an interaction force on the magnetic suspension rotor assembly 10 to finally enable the relative position between the rotor 5 and the stator body 1 to be within a set range.

The magnetic coupler stator assembly 20 includes a plurality of fan-shaped magnets, and a magnetic field arrangement of the magnetic coupler stator assembly 20 is just opposite to that of the magnetic coupler rotor assembly 11, that is, the magnetization directions the magnets of the magnetic coupler stator assembly 20 are opposite to the magnets of the magnetic coupler rotor assembly 11. The magnetic coupler stator assembly 20 for example is fixed on a rotation shaft of the electrical motor 21 and rotates under the drive of the electrical motor 21. Because of the magnetic field generated by the magnetic coupler stator assembly 20 and the magnetic coupler rotor assembly 11, an interactive torque is generated between the magnetic coupler stator assembly 20 and the magnetic coupler rotor assembly 11 so as to drive the rotor 5 to rotate.

Figure 6:
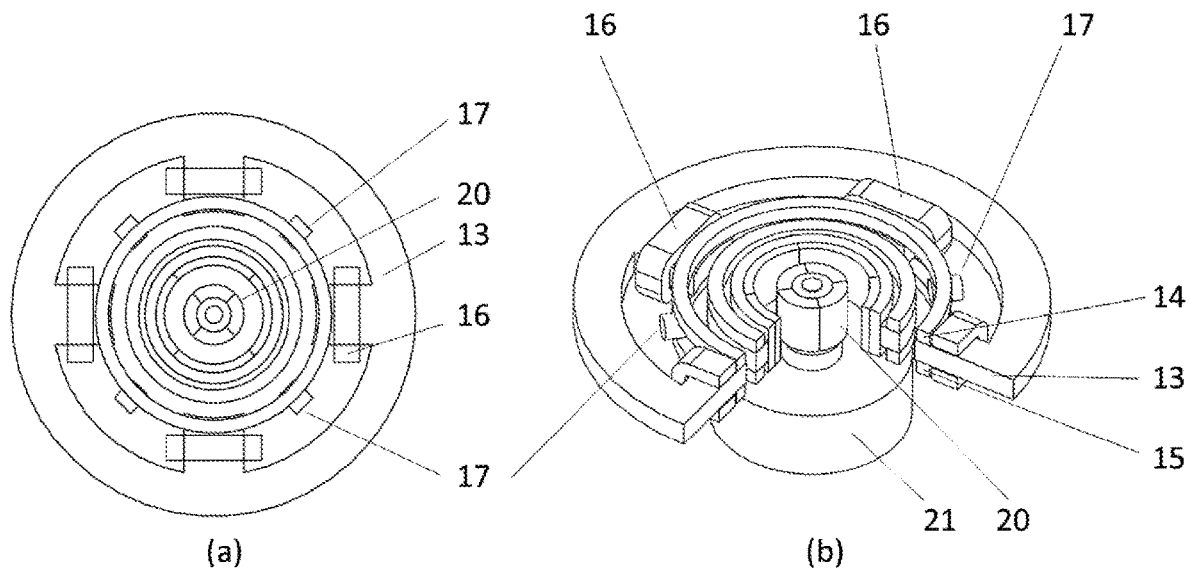
FIG. 6: the rotor and the stator

FIG. 6 illustrates the core components of the rotor illustrated in FIG. 4 and the core components of the stator illustrated in FIG. 5 together, and the core components of the rotor and the core components of the stator correspond to the overall sectional view of FIG. 3. To such an extent, the structure of the present disclosure has been clearly disclosed.

Figure 7:
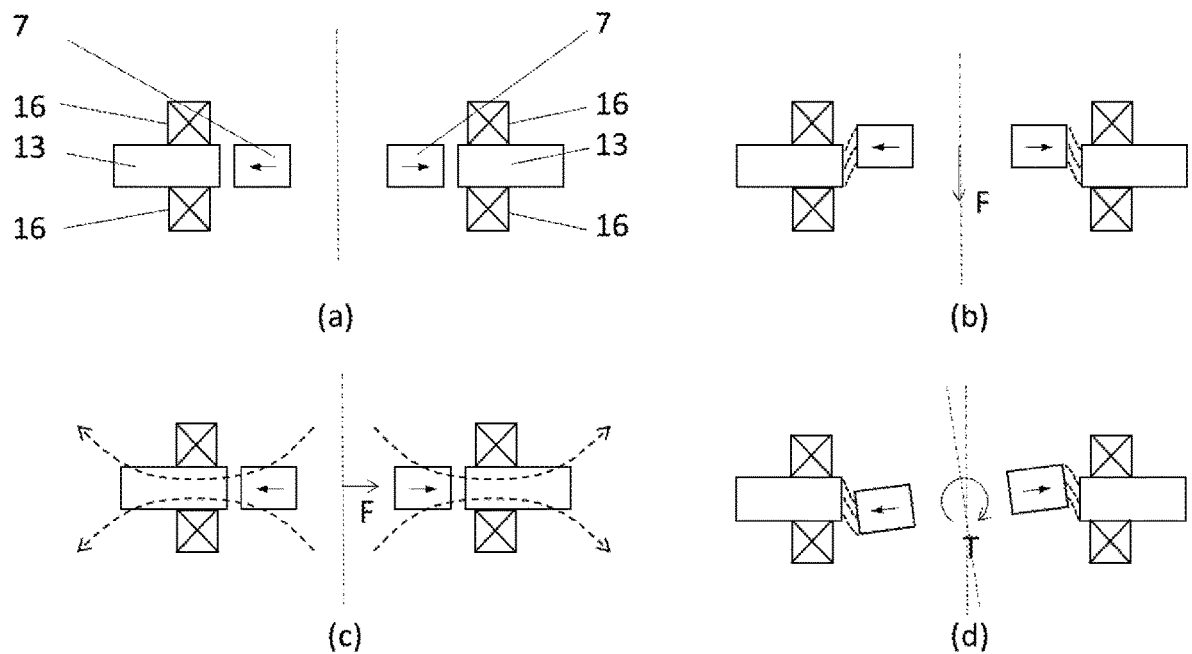
FIG. 7: a magnetic suspension assembly

FIG. 7 further explains the magnetic suspension principle of the present disclosure. FIG. 7(a), FIG. 7 (b), FIG. 7 (c) and FIG. 7 (d) show four different sectional views of the same structure including the stator core 13 and the coil 16 of the magnetic suspension stator assembly 19 and the magnetic ring 7 of the magnetic suspension rotor assembly 10, therefore, these components are numbered only in FIG. 7(a), and the components in FIG. 7 (b), FIG. 7 (c) and FIG. 7 (d) correspond to those in the FIG. 7(a) one by one. The sectional views show the components on both sides of the rotation axis. The auxiliary magnetic rings 8, 9, 14 and 15 are omitted for simplicity. Because the magnetic fields of the magnetic ring 7 are radial uni-polar magnetic fields, the strength of the magnetic fields generated in the air gap between the stator core 13 and the magnetic ring 7 are evenly distributed along the circumferential direction, and a resultant magnetic suspension force generated between the stator core 13 and the magnetic ring 7 is equal to zero. As will be known later, a total force of the magnetic coupler assembly is always equal to zero. Finally, a resultant force on the magnetic ring 7, the magnetic suspension rotor assembly 10 and the rotor 5 is equal to zero.

FIG. 7(c) shows the situation that a current passes through the coil 16. At this time, the magnetic field generated by the coil 16 in the stator core 13 and diffused into the air gap is added to the magnetic field generated by the magnetic ring 7 on one side of rotation axis and is subtracted from the magnetic field generated by the magnetic ring 7 on the other side of the rotation axis, so that the resultant magnetic field is no longer symmetrical and the resultant radial force is no longer equal to zero, resulting in a control force related to the magnitude and direction of the current in the coil 16. In FIG. 7(c), a symbol F indicates the direction of the control force generated because of the magnetic field described in the figure. The control circuit 18 detects the position of the rotor through the rotor position sensor 17 and adjusts the control force, so that the rotor 5 is always within the set position range of the stator body 1 in two radial directions, and the suspension is realized.

In the case that the rotor 5 stably suspends near the center of the stator body 1, because the magnetic fields in the circumferential air gap are circumferentially symmetrical, the resultant force of the magnetic fields generated by the permanent magnets is zero, therefore the control current in the coil 16 is also close to zero, and the magnetic suspension power consumption can be extremely low and close to zero.

In the case that gravity (an acceleration force) generates a component in the radial direction because of the inclination or acceleration of the whole pump body, the control circuit 18 enables the rotor 5 slightly to deviate from the center of the stator body 1, so that the magnetic field force generated by each permanent magnet just offsets the radial component of gravity. In this case, the control current in the coil 16 is also close to zero, and the magnetic suspension power consumption can also be extremely low and close to zero. This control manner is called zero power consumption control.

In the case that an additional periodic force caused by a periodic vibration or rotation of the rotor 5 generates a component in the radial direction, the control circuit 18 enables the rotor 5 to move periodically near the center of the stator body 1, so that the periodic magnetic field forces generated by the permanent magnets just offset the component generated by the additional periodic force in the radial direction. In this case, the control current in the coil 16 is minimized, and the magnetic suspension power consumption is also minimized, which is far less than the power consumption required by the case of simply using the electromagnetic force generated by the current in the coil 16 to resist the component of the additional periodic force in the radial direction. This control manner is called periodic zero power consumption control.

FIG. 7(b) shows that in the case that the rotor 5 is displaced relative to the stator body 1 in the axial direction, the magnetic ring 7 in the rotor 5 and the stator core 13 in the magnetic suspension stator assembly 19 are equally displaced relative each other. In this case, a magnetic field illustrated by the dotted line in FIG. 7(b) is generated in the air gap between the stator core 13 and the magnetic ring 7. This magnetic field is asymmetric in the axial direction, and generates an axial force which is indicated by the symbol F in FIG. 7(c). This axial force enables the rotor 5 to return to the initial position set by the stator body 1, and is a passive restoring force. Therefore, under the action of this passive restoring force, the rotor 5 passively and stably suspends in the one freedom degree of the axial direction.

FIG. 7(d) shows the case that the rotor 5 inclines relative to the stator body 1, the magnetic ring 7 in the rotor 5 inclines the same relative to the stator core 13 in the magnetic suspension stator assembly 19. At this time, a magnetic field illustrated by the dotted line in FIG. 7(d) is generated in the air gap between the stator core 13 and the magnetic ring 7. This magnetic field is symmetrical on both sides of the axial direction so that an axial force is equal to zero, but the magnetic field is asymmetrical relative to the inclination direction, and finally a restoring torque is generated to enable the rotor 5 return to the initial set posture, and the generated restoring torque is represented by the symbol T in FIG. 7(d). That is, under the action of this passive restoring torque, the rotor 5 passively and stably suspends in the two freedom degrees of the inclination direction.

To this extent, the magnetic suspension principle of the present disclosure has been fully explained using a simplified structure, and it is obtained that the rotor 5 is actively controlled and stably suspends in two radial freedom degrees, and passively and stably suspends in one axial freedom degree and in two inclined freedom degrees. As a rigid body, the rotor 5 has 6 freedom degrees, and 5 freedom degrees are stably suspended as described above.

In the case of actively controlling the freedom degree of suspension, the zero power consumption control manner and the periodic zero power consumption control manner are used, which enables the power consumption of magnetic suspension to be significantly reduced and close to zero. In the case of passively and stably controlling the freedom degree of suspension, power is not consumed.

Figure 8:
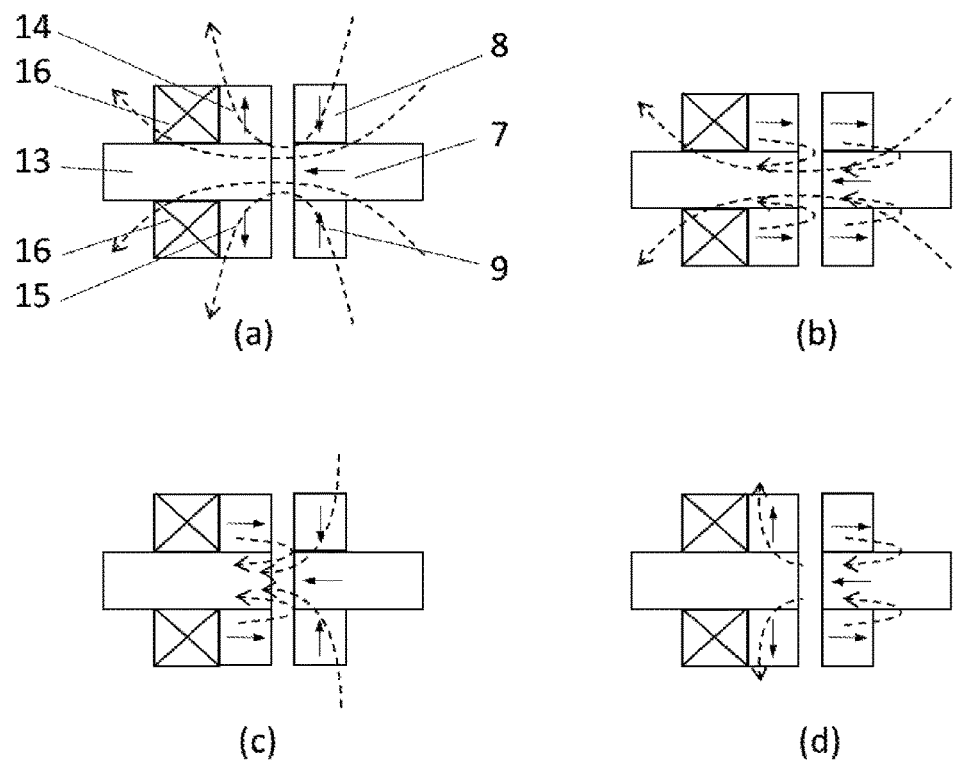
FIG. 8: various structures of the magnetic suspension assembly

FIG. 8(a) shows the structure including the auxiliary magnetic rings 8, 9, 14 and 15, which further enhances the magnetic field in the air gap and improves the efficiency of suspension. FIG. 8(a), FIG. 8 (b), FIG. 8(c) and FIG. 8(d) respectively show cross-sectional views of the same structure including the stator core 13 and coil 16 in the magnetic suspension stator assembly 19, the magnetic ring 7 in the magnetic suspension rotor assembly 10, and the auxiliary magnetic rings 8, 9, 14 and 15, thus these components are numbered only in FIG. 8(a), and the components in FIG. 8 (b), FIG. 8(c) and FIG. 8(d) respectively correspond to the components in FIG. 8(a) one by one. These cross-sectional views only show the structure on one side of the rotation axis. The auxiliary magnetic rings 14 and 15 are additionally arranged on the stator core 13 of the magnetic suspension stator assembly 19 on the other side of the rotation axis, and the auxiliary magnetic rings 8 and 9 are additionally arranged on the magnetic ring 7 of the magnetic suspension rotor assembly 10 on the other side of the rotation axis. These auxiliary magnetic rings may be set independently or may be removed, and the basic principle of providing the auxiliary magnetic rings is that: the magnetic field generated in the air gap between the stator core 13 and the magnetic ring 7 by each auxiliary magnetic ring is added with the magnetic field generated in the air gap by the magnetic ring 7 to enhance the magnetic field generated by the magnetic ring 7. The term "added with" herein refers to that the magnetic field generated in the air gap by each magnetic ring have the same direction as that of the magnetic field generated in the air gap by the magnetic ring 7, and the amplitude of the magnetic field obtained after adding the above-mentioned magnetic fields with each other is increased.

Based on the basic principle that the magnetic field generated in the air gap by each auxiliary magnetic ring is added with the magnetic field generated by the magnetic ring 7, there are several examples of the magnetic ring magnetization direction and arrangement schemes illustrated in FIG. 8 (b), FIG. 8(c) and FIG. 8(d). A variety of arrangement schemes are illustrated in FIG. 8, which illustrates the basic principle that the magnetic field generated by the auxiliary magnetic ring and the magnetic field generated by the magnetic ring 7 are added in the air gap under different magnetization configurations of the auxiliary magnetic rings. In the configuration scheme illustrated in FIG. 8(a) and FIG. 8(b), magnetic force lines representing the magnetic field generated by the magnetic ring 7 and magnetic force lines representing the magnetic field generated by the auxiliary magnetic rings are simultaneously drawn. FIG. 8(c) and FIG. 8(d) only show the magnetic force lines representing the magnetic field generated by the auxiliary magnetic rings. It can be seen that in these configuration schemes, the magnetic force lines representing the magnetic field generated by each auxiliary magnetic ring is added in the air gap with the magnetic force lines representing the magnetic field generated by the magnetic ring 7. It should be understood that by reversing or rotating the magnetization directions of the magnetic ring 7 and the auxiliary magnetic rings illustrated in FIG. 8, or by any substitution and combination of the structures illustrated in FIG. 8, a variety of configuration schemes that satisfy the addition of the magnetic fields in the air gap can be obtained. To this extent, the basic principle of the arrangement of the auxiliary magnetic rings is completely described. For reasons of simplicity, all the arrangement schemes are not listed here, but other combinations can be listed by ordinary technicians in the art based on the disclosure.

The last freedom degree of the rotor 5 that is required to be controlled is a rotation freedom degree, and the control of the rotation freedom degree is realized by the magnetic coupler.

Figure 9:
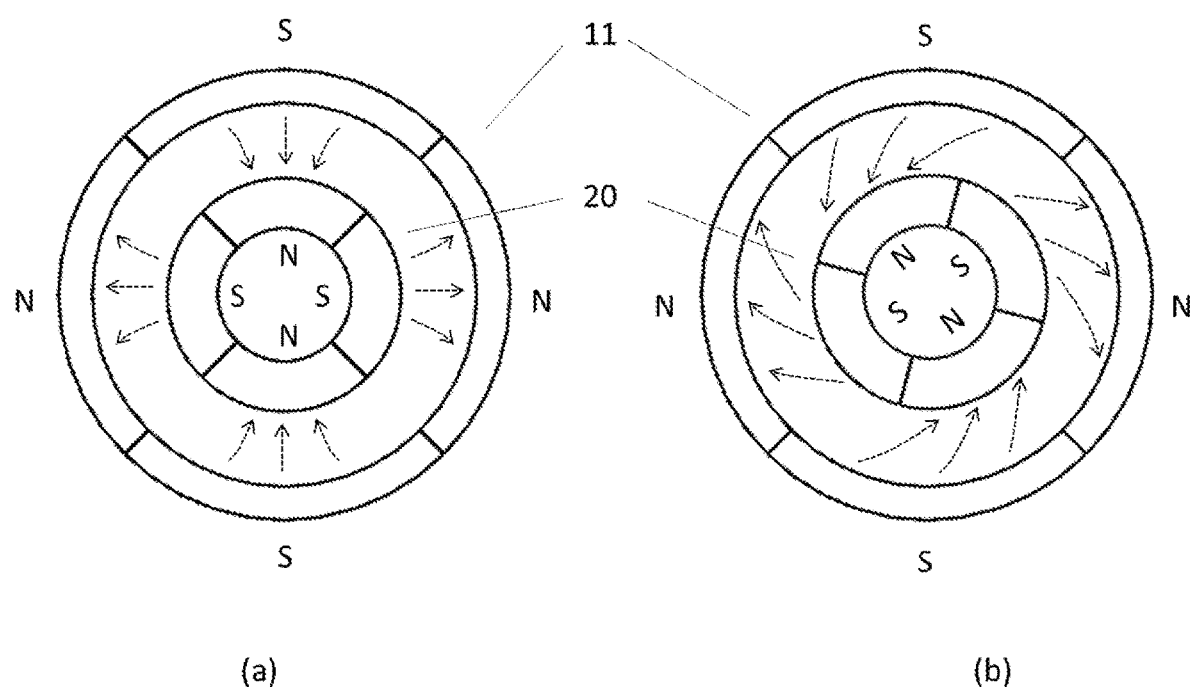
FIG. 9: a magnetic coupler assembly

FIG. 9 shows a magnetic coupler assembly including the magnetic coupler stator assembly 20 and the magnetic coupler rotor assembly 11. The magnetic coupler stator assembly 20 generates the periodic multi-polar magnetic fields distributed along the circumferential direction, and the distribution of the magnetic fields generated by the magnetic coupler rotor assembly 11 is just opposite to that of periodic multi-polar magnetic fields generated by the magnetic coupler stator assembly 20. In the case that the relative angular displacement between the magnetic coupler stator assembly 20 and the magnetic coupler rotor assembly 11 is equal to zero as illustrated in FIG. 9(a), the magnetic force lines between the magnetic coupler stator assembly 20 and the magnetic coupler rotor assembly 11 periodically alternate in the circumferential direction as illustrated by the dashed lines in FIG. 9(a), and the magnetic force lines for each magnetic pole are symmetrically distributed in the circumferential direction, therefore the resultant force and the resultant torque are all equal to zero. In the case that the relative angular displacement between the magnetic coupler stator assembly 20 and the magnetic coupler rotor assembly 11 is not equal to zero as illustrated in FIG. 9(b), the magnetic force lines between the magnetic coupler stator assembly 20 and the magnetic coupler rotor assembly 11 alternate periodically in the circumferential direction as illustrated by the dashed lines in FIG. 9(b), but always turn to a same side for each magnetic pole in the circumferential direction. In this case, the resultant force is equal to zero but the resultant torque is not equal to zero. Therefore, the magnetic coupler transfers the torque between the stator and the rotor, and the magnitude of the transferred torque is related to the relative angular displacement between the magnetic coupler stator assembly 20 and the magnetic coupler rotor assembly 11. The magnetic coupler stator assembly 20 for example is fixed on the shaft of the electrical motor 21, therefore when the electrical motor 21 rotates, the electrical motor 21 drives the rotor 5 and the impeller 6 to rotate, and then drive the fluid in the volute 2 to move. To this extent, completely controllable suspension and rotation of all six freedom degrees of the rotor 5 are realized.

The magnetic coupler transfers the torque completely through the permanent magnets. In the case that the operation speed of the fluid pump is far lower than the speed of light in a medium, the energy loss in the process of torque transmission is extremely low compared with the energy required by the pump, and can be considered as zero.

Finally, that magnetic suspension stator assembly 19 and the magnetic suspension rotor assembly 10 constitute the magnetic suspension assembly which generates the radial uni-polar magnetic poles and magnetic fields along the circumferential direction, and the function of the magnetic suspension assembly is to realize magnetic suspension of the rotor 5. The magnetic coupler stator assembly 20 and the magnetic coupler rotor assembly 11 constitute the magnetic coupler assembly which generates the radial non-zero even periodic magnetic poles and magnetic fields along the circumferential direction, and the function of the magnetic coupler assembly is to drive the rotor to rotate.

The above embodiments fully disclose the magnetic suspension principle and the rotation drive principle of the present disclosure. According to the magnetic coupling suspension pump disclosed by the disclosure, the rotor 5 and the volute 2 do not have any mechanical friction and shear, do not need any mechanical bearings and dynamic seals, effectively avoid leakage and pollution, and have high reliability. When the rotor 5 rotates stably, the power consumption of magnetic suspension is extremely low and close to zero. The magnetic coupler has no energy loss in the process of torque transmission. Therefore, almost all the output power of the electrical motor 21 is used to drive the fluid, and the efficiency of the whole machine is very high.

As an alternative scheme, the stator assembly 20 of the magnetic coupler for example is replaced by a stator winding of the electrical motor wound with multiphase coils, and the stator winding is arranged at the same position as the stator assembly 20. For the stator winding of the electrical motor, when currents with phase difference are introduced into the multiphase coils, a rotation magnetic field is generated in the space by the multiphase coils; and the torque generated by the rotation magnetic field of the multiphase coils, on the magnetic coupler rotor assembly 11 has the same effect compared with that of the rotation magnetic field generated by magnetic coupler stator assembly 20 which rotates mechanically. The electrical motor stator winding and the magnetic coupler rotor assembly 11 actually constitute a permanent magnet electrical motor. The efficiency of the permanent magnet electrical motor is lower than that of the electrical motor 21 in the case that the rotor 5 is driven to rotate by the magnetic coupler stator assembly 11, because the air gap between the stator and the rotor of the permanent magnet electrical motor is generally large. However, in some special occasions, such as implantable medical devices such as artificial heart, nuclear energy or aerospace, it is desirable to completely avoid mechanical components such as bearings, this alternative scheme may be adopted.

The above is only the preferred embodiments of the present invention, and is not used to limit the present disclosure. It should be pointed out that for ordinary technicians in the art, without departing from the technical principle of the present invention, several improvements and variations may be made, and these improvements and variations should also be regarded as the protection scope of the present disclosure.

What is claimed is:

1. A magnetic coupling suspension pump, comprising a stator body and a rotor, wherein
   the stator body comprises a magnetic suspension stator assembly and a magnetic coupler stator assembly;
   the rotor comprises a magnetic suspension rotor assembly and a magnetic coupler rotor assembly;
   the magnetic suspension stator assembly and the magnetic suspension rotor assembly constitute a magnetic suspension assembly, and the magnetic suspension assembly is configured to generate radial uni-polar magnetic poles and magnetic fields arranged along a circumferential direction, resulting in that the rotor suspends;
   the magnetic coupler stator assembly and the magnetic coupler rotor assembly constitute a magnetic coupler assembly, and the magnetic coupler assembly is configured to generate radial non-zero even number of periodic magnetic poles and magnetic fields arranged along the circumferential direction, resulting in that the rotor rotates; and
   the magnetic coupler rotor assembly comprises any non-zero even number of magnets arranged along the circumferential direction, the magnetic coupler stator assembly comprises any non-zero even number of magnets arranged along the circumferential direction, and a magnetic field arrangement mode of the non-zero even number of magnets of the magnetic coupler stator assembly is opposite to a magnetic field arrangement mode of the non-zero even number of magnets of the magnetic coupler rotor assembly.

2. The magnetic coupling suspension pump according to claim 1, wherein
   the magnetic suspension assembly is configured that two radial freedom degrees of suspension of the rotor are actively controlled, a axial freedom degree of suspension of the rotor is passively controlled and two inclined freedom degrees of suspension of the rotor are passively suspended; and
   the magnetic coupler assembly drives the rotor to rotate, the rotor does not have any mechanical contact with the stator body when the rotor rotates.

3. The magnetic coupling suspension pump according to claim 1, wherein
   the magnetic suspension rotor assembly comprises a magnetic ring, the magnetic suspension stator assembly comprises a stator core, and the stator core surrounds the magnetic ring; and
   a magnetization direction of the magnetic ring is along a radial direction of the rotor and faces towards or away from the stator core.

4. The magnetic coupling suspension pump according to claim 3, wherein
   the magnetic suspension rotor assembly further comprises auxiliary magnetic rings which are respectively on an upper side and a lower side of the magnetic ring in an axial direction of the rotor;
   the magnetic suspension stator assembly further comprises auxiliary magnetic rings which are respectively on an upper side and a lower side of the stator core in an axial direction of the stator body; and
   the auxiliary magnetic rings of the magnetic suspension rotor assembly and the auxiliary magnetic rings of the magnetic suspension stator assembly are configured that a magnetic field generated by each auxiliary magnetic ring in an air gap between the stator core and the magnetic ring is added with a magnetic field generated by the magnetic ring in the air gap, and the "added with" refers to that the magnetic fields added with each other have a same direction and an amplitude of a magnetic field obtained after adding the magnetic fields with each other is increased.

5. The magnetic coupling suspension pump according to claim 4, wherein the magnetic ring and the auxiliary magnetic rings of the magnetic suspension rotor assembly are made of a permanent magnet material.

6. The magnetic coupling suspension pump according to claim 4, wherein
   a magnetization direction of the auxiliary magnetic ring on the upper side of the magnetic ring and a magnetization direction of the auxiliary magnetic ring on the lower side of the magnetic ring are both along the axial direction of the rotor and are opposite to each other; or,
   the magnetization direction of the auxiliary magnetic ring on the upper side of the magnetic ring and the magnetization direction of the auxiliary magnetic ring on the lower side of the magnetic ring are both along the radial direction of the rotor and are same with each other.

7. The magnetic coupling suspension pump according to claim 4, wherein
   the magnetization direction of the magnetic ring of the magnetic suspension rotor assembly is along the radial direction of the rotor and faces towards the stator core; and
   the auxiliary magnetic rings of the magnetic suspension rotor assembly and the auxiliary magnetic rings of the magnetic suspension stator assembly are arranged in one of the following ways:
   (1) a magnetization direction of the auxiliary magnetic ring on the upper side of the magnetic ring is along the axial direction of the rotor downwardly, a magnetization direction of the auxiliary magnetic ring on the lower side of the magnetic ring is along the axial direction of the rotor upwardly, a magnetization direction of the auxiliary magnetic ring on the upper side of the stator core is along the axial direction of the stator body upwardly, and a magnetization direction of the auxiliary magnetic ring on the lower side of the stator core is along the axial direction of the stator body downwardly;

(2) the magnetization direction of the auxiliary magnetic ring on the upper side of the magnetic ring and the magnetization direction of the auxiliary magnetic ring on the lower side of the magnetic ring are both along the radial direction of the rotor in a same direction and are both opposite to the magnetization direction of the magnetic ring, and the magnetization direction of the auxiliary magnetic ring on the upper side of the stator core and the magnetization direction of the auxiliary magnetic ring on the lower side of the stator core are both along the radial direction of the stator body in a same direction and both face towards the rotor;

(3) the magnetization direction of the auxiliary magnetic ring on the upper side of the magnetic ring is along the axial direction of the rotor downwardly, the magnetization direction of the auxiliary magnetic ring on the lower side of the magnetic ring is along the axial direction of the rotor upwardly, and the magnetization direction of the auxiliary magnetic ring on the upper side of the stator core and the magnetization direction of the auxiliary magnetic ring on the lower side of the stator core are both along the radial direction of the stator body in a same direction and both face towards the rotor; and (4) the magnetization direction of the auxiliary magnetic ring on the upper side of the magnetic ring and the magnetization direction of the auxiliary magnetic ring on the lower side of the magnetic ring are both along the radial direction of the rotor in a same direction and are both opposite to the magnetization direction of the magnetic ring, the magnetization direction of the auxiliary magnetic ring on the upper side of the stator core is along the axial direction of the stator body upwardly, and the magnetization direction of the auxiliary magnetic ring on the lower side of the stator core is along the axial direction of the stator body downwardly.

8. The magnetic coupling suspension pump according to claim 3, wherein
the magnetic suspension stator assembly further comprises a control circuit, a rotor position sensor and a coil;
the rotor position sensor detects a relative position between the rotor and the stator body, and the control circuit calculates and controls a magnitude and a direction of a current in the coil according to the relative position to generate a magnetic field in the stator core, and the magnetic field in the stator core generates an interaction force on the magnetic suspension rotor assembly so that the rotor suspends.

9. The magnetic coupling suspension pump according to claim 8, wherein
by controlling the magnitude and the direction of the current in the coil, the control circuit adjusts the relative position between the rotor and the stator body, so that the magnetic ring generates a radial constant force on the rotor to resist an external radial force and realize a zero power consumption control; and
by controlling the magnitude and the direction of the current in the coil, the control circuit by controlling the magnitude and the direction of the current in the coil, the control circuit periodically adjusts the relative position between the rotor and the stator body, so that the magnetic ring generates a radial periodic force on the rotor to resist an external periodic radial force and realize a periodic zero power consumption control.

10. The magnetic coupling suspension pump according to claim 4, wherein
the magnetic suspension stator assembly further comprises a control circuit, a rotor position sensor and a coil;
the rotor position sensor detects a relative position between the rotor and the stator body, and the control circuit calculates and controls a magnitude and a direction of a current in the coil according to the relative position to generate a magnetic field in the stator core, and the magnetic field in the stator core generates an interaction force on the magnetic suspension rotor assembly so that the rotor suspends.

11. The magnetic coupling suspension pump according to claim 10, wherein
by controlling the magnitude and the direction of the current in the coil, the control circuit adjusts the relative position between the rotor and the stator body, so that the magnetic ring, the auxiliary magnetic rings of the magnetic suspension rotor assembly and the auxiliary magnetic rings of the magnetic suspension stator assembly generate a radial constant force on the rotor to resist an external radial force and realize a zero power consumption control; and
by controlling the magnitude and the direction of the current in the coil, the control circuit by controlling the magnitude and the direction of the current in the coil, the control circuit periodically adjusts the relative position between the rotor and the stator body, so that the magnetic ring, the auxiliary magnetic rings of the magnetic suspension rotor assembly and the auxiliary magnetic rings of the magnetic suspension stator assembly generate a radial periodic force on the rotor to resist an external periodic radial force and realize a periodic zero power consumption control.

12. The magnetic coupling suspension pump according to claim 1, wherein the magnetic field arrangement mode of the non-zero even number of magnets of the magnetic coupler rotor assembly along the circumferential direction is that magnetization directions of two adjacent magnets rotate 180 degrees or 90 degrees with respect to each other.

13. The magnetic coupling suspension pump according to claim 12, wherein
the non-zero even number of magnets of the magnetic coupler rotor assembly are a plurality of fan-shaped permanent magnets, and the plurality of fan-shaped permanent magnets are the same with each other in size; and
the non-zero even number of magnets of the magnetic coupler stator assembly are a plurality of fan-shaped permanent magnets, and the plurality of fan-shaped magnets are the same with each other in size.

14. The magnetic coupling suspension pump according to claim 12, wherein magnetization directions of the non-zero even number of magnets of the magnetic coupler rotor assembly are arranged to generate periodic multi-polar magnetic fields that are superimposed to be enhanced on one side of the magnetic coupler rotor assembly while are superimposed to be weakened on the other side of the magnetic coupler rotor assembly.

15. The magnetic coupling suspension pump according to claim 14, wherein the magnetization directions of the non-zero even number of magnets of the magnetic coupler rotor assembly are sequentially arranged in a manner of ↑ → ↓ ← ↑ → ↓ ← . . . .

16. The magnetic coupling suspension pump according to claim 1, wherein the rotor further comprises a magnetic conduction ring, the magnetic conduction ring is between the magnetic suspension rotor assembly and the magnetic coupler rotor assembly in the radial direction of the rotor to provide a closed loop respectively for magnetic flux of the magnetic suspension rotor assembly and magnetic flux of the magnetic coupler rotor assembly, and simultaneously isolate the magnetic field of the magnetic suspension rotor assembly from the magnetic field of the magnetic coupler rotor assembly so that the magnetic suspension rotor assembly and the magnetic coupler rotor assembly do not interfere with each other.

17. The magnetic coupling suspension pump according to claim 1, wherein
the stator body further comprises an electrical motor; and
the magnetic coupler stator assembly is an electrical motor stator winding wound with multiphase coils, and currents with phase difference are introduced into the multiphase coils of the electrical motor stator winding to generate a spatial rotation magnetic field to drive the magnetic coupler rotor assembly to rotate.

18. The magnetic coupling suspension pump according to claim 1, wherein
the stator body further comprises an electrical motor;
the magnetic coupler stator assembly is fixed on a rotation shaft of the motor, rotates together with the rotation shaft driven by the electrical motor, and transmits torque to the magnetic coupler rotor assembly, so that the magnetic coupler rotor assembly drives the rotor to rotate.

19. The magnetic coupling suspension pump according to claim 1, wherein
the magnetic suspension stator assembly, the magnetic coupler stator assembly, the magnetic suspension rotor assembly and the magnetic coupler rotor assembly all surround a central axis of the stator body; and
the magnetic coupler stator assembly, the magnetic coupler rotor assembly, the magnetic suspension rotor assembly and the magnetic suspension stator assembly are sequentially arranged from inside to outside along the radial direction of the stator body.

20. The magnetic coupling suspension pump according to claim 1, further comprising a volute, wherein
the volute is connected with the stator body, the rotor is in a space defined by the volute and the stator body, and the rotor does not have any mechanical contact with the volute during when the rotor rotates;
the stator body and the volute are configured as an integral structure or are configured be separable from each other;
the volute comprises a fluid inlet and a fluid outlet;
the rotor further comprises an impeller, the impeller pushes a fluid flowing into the volute through the fluid inlet to the fluid outlet when the rotor rotates, and the fluid fills a space between an inner wall of the volute and the rotor during the fluid flows in the volute; and
the fluid inlet of the volute and the fluid outlet of the volute are on a same side of the stator body.

* * * * *